United States Patent [19]

Taus

[11] 4,301,808
[45] Nov. 24, 1981

[54] PULSE RATE MONITOR

[76] Inventor: Herbert G. Taus, 451 Ridge Run, Centre Square, Pa. 19422

[21] Appl. No.: 95,321

[22] Filed: Nov. 19, 1979

[51] Int. Cl.³ ............................................. A61B 5/02
[52] U.S. Cl. ................................. 128/687; 128/689
[58] Field of Search ............................. 128/633–634, 128/665–667, 687–690

[56] References Cited

U.S. PATENT DOCUMENTS

| | | | |
|---|---|---|---|
| 2,790,438 | 4/1957 | Taplin et al. | 128/633 |
| 3,638,640 | 2/1972 | Shaw | 128/633 |
| 3,810,460 | 5/1974 | Van Nie | 128/666 |
| 3,815,583 | 6/1974 | Scheidt | 128/666 |
| 3,980,075 | 9/1976 | Heule | 128/666 |
| 3,993,047 | 11/1976 | Peek | 128/666 |

Primary Examiner—Robert W. Michell
Assistant Examiner—Francis J. Jaworski
Attorney, Agent, or Firm—Eugene E. Renz, Jr.

[57] ABSTRACT

An improved pulse rate monitoring system for detecting and displaying the heart beat of a subject while exercising or performing other activities. The subject invention comprises a pair of infrared emitters adapted to be positioned on either side of a thin appendage of the body, such as the septum of the nose or the upper part of an ear. The emitter light paths are modulated by changes in the superficial blood volume in these areas, causing corresponding changes in the output of these emitters as sensed by an infrared detector. The emitters are power strobed to provide a pulsed sensor output which is processed by electronic means to provide both analog and digital displays for use by the exerciser. The unit further comprises a visual pulse output which blinks on and off at a rate corresponding to the exerciser's heartbeat. The unit further comprises means for setting high and low levels which when exceeded will provide an audio output to warn the exerciser in time to take corrective measures in his exercise regime.

15 Claims, 10 Drawing Figures

PULSE RATE MONITOR

BACKGROUND OF THE INVENTION

1. Field of the Invention

This invention relates to blood pulse monitors and in particular to monitors which sense changes of blood volume through light sources and sensors in contact with the surface of the skin.

2. Description of the Prior Art

The need for proper and adequate exercise for both healthy persons and those with cardiac afflications is becoming more widely understood. With this new knowledge cardiologists, internists, general practitioners, and other physicians are prescribing exercise for the healthy as well as for those with heart problems. In addition, the general public is responding by participating in individual exercise programs such as tennis, biking, jogging, etc. This represents a significant trend away from traditional exercise routines, where they were previously practiced, for the most part, on a dedicated amateur or professional basis. Thus, the great majority of exercise was formerly handled on a planned and supervised basis which provided for control of the level of exercise. Even with that control, exercise physiologists are now finding that better control of amateur and professional exercise can dramatically improve results in a shorter period of time. Thus, control methods are starting to be used for organized exercise programs. This control can be achieved through normal physiological internal indicators such as fatigue or through external instrumentation monitoring pulse rate. Fatigue indications are usually adequate to insure that the exerciser does not injure himself, however, this does not insure proper amounts or levels of exercise, which is the main purpose of the program. The reasons for this are that the person may over-exercise during the beginning of the session and thus, not sustain his efforts long enough to be effective; the person may under-exercise but the fatigue symptoms resulting from the exercise may be so uncomfortable that he is discouraged from continuing further. Lastly, the level of effort to achieve acceptable exercise tends to change with factors such as general physical conditioning, fatigue level, ambient temperature and humidity, and emotional state. Monitoring pulse rate has been found to be an effective way of monitoring the adequacy of an exercise program.

Most instruments available on the market today for monitoring pulse rate, detect the heart beat by monitoring electrical signals emanating from the heart (electrocardiogram). In practice, it has been found that there are several serious drawbacks affecting the utility of these devices. These include the necessity for a good electrical contact between the body and instrument in order to reliably monitor electrocardiographic signals on a continuing basis. Furthermore, electrocardiographic techniques which assure good electrical contact require body electrodes which have to be changed periodically. These electrodes can also cause severe skin irritations. Ambulatory electrocardiographic techniques, while possible, are difficult with obese people and females with pendulous breasts. A single electrode configuration, as used for exercise monitoring, will not work on all people because of differences in the orientation of the electrical axis of the heart, especially in people who have suffered a heart attack. Lastly, the use of electrocardiographic techniques in colder climates can be inconvenient because of clothing problems. Because of the shortcomings related to electrocardiographic techniques, new techniques for monitoring pulse rate are required.

Recently, it has been found that pulse rate monitoring using light sensing techniques offers a simple and accurate approach to the problem. However, commercial devices based on this method have not been reliable because of problems associated with limitations in sensor technology, particularly those caused by ambient light, motion artifacts and, most importantly, inconsistent sensor behavior. Consequently, it has been observed that these units work inconsistently on some people and not at all on others. Some of these problems are overcome when infrared rather than visible light is used. The skin is somewhat transparent to infrared and so blood volume changes related to pulse rate can be monitored more easily. However, the basic problems with such devices still remain. The present invention is designed to correct the problems and provide a more reliable, lower cost instrument for the dynamic measurement of the pulse by a user or a medical professional.

SUMMARY OF THE INVENTION

The principle employed in the present invention is that of monitoring the cyclic changes in superficial blood volume in and under the skin as a function of changes in blood pressure and correlating these with the pulse. The specific technique is the generation of an oscillatory voltage by a sensor which is detecting infrared radiation which has either passed through or been reflected from a body appendage such as an ear. The radiation intensity observed is a function of blood volume changes which in turn are related to regular changes in blood pressure from systolic to diastolic conditions at the beginning and end of each cycle. As a result of this regular variation, the sensor output can be either used as an analog representation of the blood pressure waeform or converted to a series of pulses, one for each heart beat. These pulses, with suitable logic, can be clocked so that a rate in terms of pulse/minute can be calculated. This, in turn, can be displayed either in analog form on a meter or digitally.

The present invention contains features or characteristics which are specifically designed to minimize or preclude the three disadvantages of current light pulse monitoring systems i.e. ambient light, motion artifacts, and inconsistent behavior. The measures taken to overcome these disadvantages are not mutually exclusive, but are best understood when explained as independent features.

Extraneous light sources which can enter the detector causing faulty operation are prevented from entering the detector by maintaining the photo-detector and the light source in intimate contact with the body. This tends to produce a light-tight path from the emitter (source) to the detector. To further enhance sensitivity, the emitter/detector area is surrounded by a shield which prevents all but tangential light rays from entering the emitter/detector path. Coatings and paints which absorb rather than reflect energy in the visible light or infrared spectrum are used throughout.

Manufactured with light-weight materials, the mass of the assembly has been minimized tending to eliminate or reduce motion artifacts. Connections between assemblies are made with thin, flexible, stress relieved wires to minimize tension forces further reducing motion artifacts.

Inconsistent sensor behavior from person to person and at different times on the same person is appreciably minimized or eliminated by the following five design features. First, the use of two light sources, one for transmission and the other for reflection, improves signal level on all people but also reduces the signal level spread from person to person and from day to day on the same person. Secondly, pulsing the light source improves the signal level thus reducing the effects of external light sources. This also has the beneficial effect of prolonging battery life. Thirdly, optimum signal level is obtained by adjusting the pressure applied by the two sides of the sensing/detecting element to the body at the point of contact. The effect is to allow proper flow of blood in the region of the active components and simultaneously maintain good contact for light tightness. Fourth, further signal level improvements are obtained in the electronic circuitry by limiting low and high level frequency responses to reduce noise and motion artifacts. Lastly, automatic gain control (AGC) prevents both noise and motion artifacts from being detected as rate signals when a voltage comparator is used for wave shaping. This eliminates the need for a difficult manual control.

The utility of this device is further enhanced by the use of a visual pulse signal which assures the user that a pulse is being detected when the sensor is attached and that motion artifacts are not interfering with sensor operation. Further warning signals can be provided which allow the user to preset high and low pulse rate limits, which when exceeded will cause an alarm to sound to warn the user of potentially dangerous heart stress at high pulse rates and that the activity level is inadequate at low pulse rates.

Accordingly, it is an object of the present invention to provide a pulse rate monitoring system comprising a sensor assembly and an electronic package assembly which is of simplified construction, lightweight and self-contained so that it may be easily and unobtrusively worn by a person exercising.

A further object of the present invention is to provide a pulse rate monitoring system characterized by novel features of construction and arrangement to minimize motion artifacts which normally result in erroneous readings.

Another object of the present invention is to provide a pulse rate monitoring system wherein the sensor and electrical package assembly include novel features which improve the accuracy of the pulse rate reading including a sensor incorporating at least two light sources, one for reflection and one for transmission light.

Still another object of the present invention is to provide a system wherein the light source is pulsed which results in an improved signal level.

A further object of the present invention is to provide a pulse rate monitoring system wherein the sensor assembly includes means for selectively adjusting the pressure applying relation of the sensor heads against the body areas to allow proper flow of blood in the region of the active components of the sensor heads and simultaneously maintain good light conduction.

A still further object of the present invention is to provide a band pass filter in the electronic circuitry of the electronic package to limit noise and motion artifacts.

A still further object of the present invention is to provide a pulse rate monitoring system which is particularly adapted for use with infrared radiation and nevertheless, may be easily modified to utilize visible light.

These objects and other objects of the present invention are hereinafter set forth more fully with reference to the accompanying drawings.

BRIEF DESCRIPTION OF THE DRAWINGS

FIG. 10 is a detailed circuit diagram including the audio, limits and digital portions of the electronic package.

DETAILED DESCRIPTION OF THE INVENTION

Figure 1:
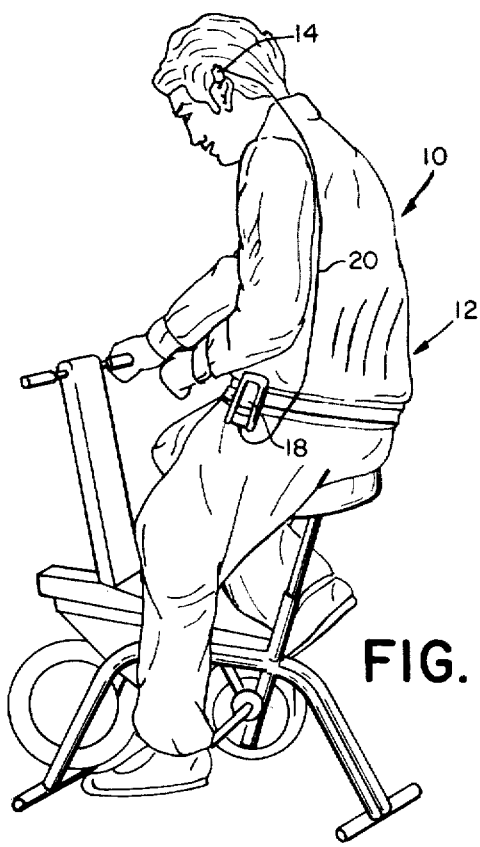
FIG. 1 is a pictorial display showing the subject invention in use.

Referring now to FIG. 1, we see a typical illustration of the subject invention in use by an exerciser 12. The pulse monitoring system consists of the sensor assembly 14 and the electronic package assembly 18 connected by a thin, flexible, stress relieved cable 20 disposed between the sensor and electronic assembly. The entire system weighing only a few ounces, is powered by small batteries and is generally worn by the subject or attached to the exercise equipment. In normal use, pulse rate is automatically indicated without prior settings or adjustments.

As shown, the sensor assembly 14 is attached to the ear 16 of the exerciser and the electronic package assembly 18 is attached to his belt. The method of attaching sensor assembly 14 to the ear is shown in detail in FIG. 2. Near the end of wire 20 there is a clip 22 which attaches to an earpiece 24 of a pair of glasses worn by the exerciser. The attachment could just as well be made on a head band, hat or some other article of clothing or equipment worn by the exerciser. The loop in wire 20 between the sensor assembly and the clip 22 serves to isolate the sensor assembly 114 from physical stresses imposed by the total weight of wire 20 which if unrelieved would tend to change the physical relationship between the ear and the sensor. This change could degrade the signals leading to incorrect pulse rate values. Sensor assembly 14 is shown attached to the upper area of ear 16. While the unit will work equally well attached to the lobe or to other appendages such as the septum of the nose or the web between the thumb and forefinger of the hand, this position has the advantage of convenience, good signal level, and rigidity of tissue.

All of these factors tend to optimize the sensor performance. In normal operation with sensor assembly 14 attached to the exerciser's or subject's ear and with the unit turned "on", the emitter/detector light path is modulated by the ebb and flow of blood through the ear. The signal is conducted to the electronic package assembly 18 through wire 20 where it is amplified, filtered, converted to digital counts and shown on a display. Audio signal setting for high and low pulse rates can be made to warn the exerciser when the limits have been exceeded.

Figure 4:
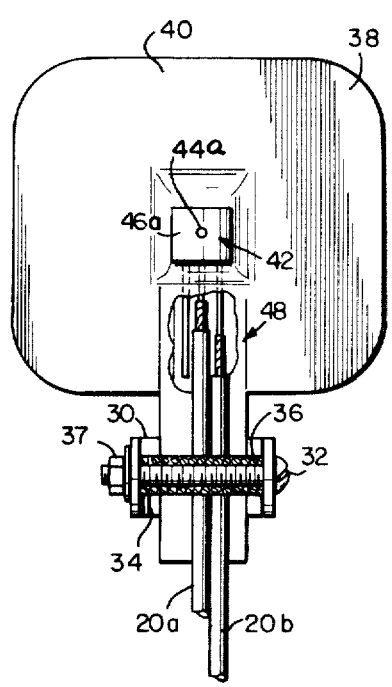
FIG. 4 is a sectional view of the sensor assembly as viewed on lines 4—4 of FIG. 3.
Figure 3:
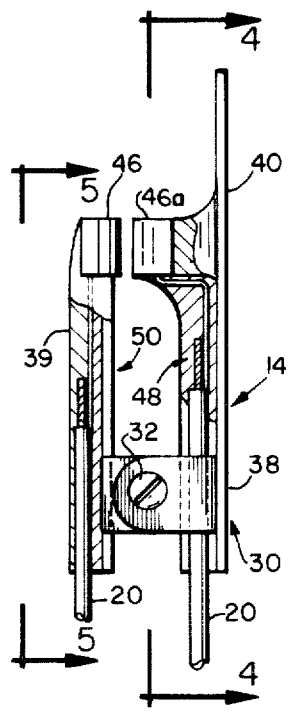
FIG. 3 is a side elevational view showing structure details of the sensor assembly.
Figure 5:
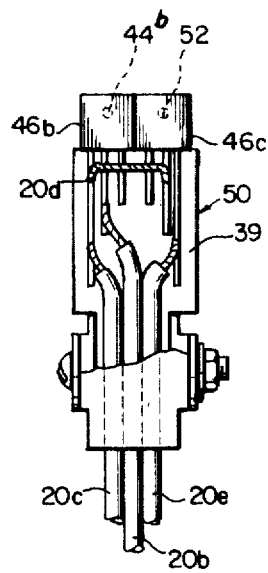
FIG. 5 is a sectional view of the sensor assembly as viewed on lines 5—5 of FIG. 3.
Figure 6:
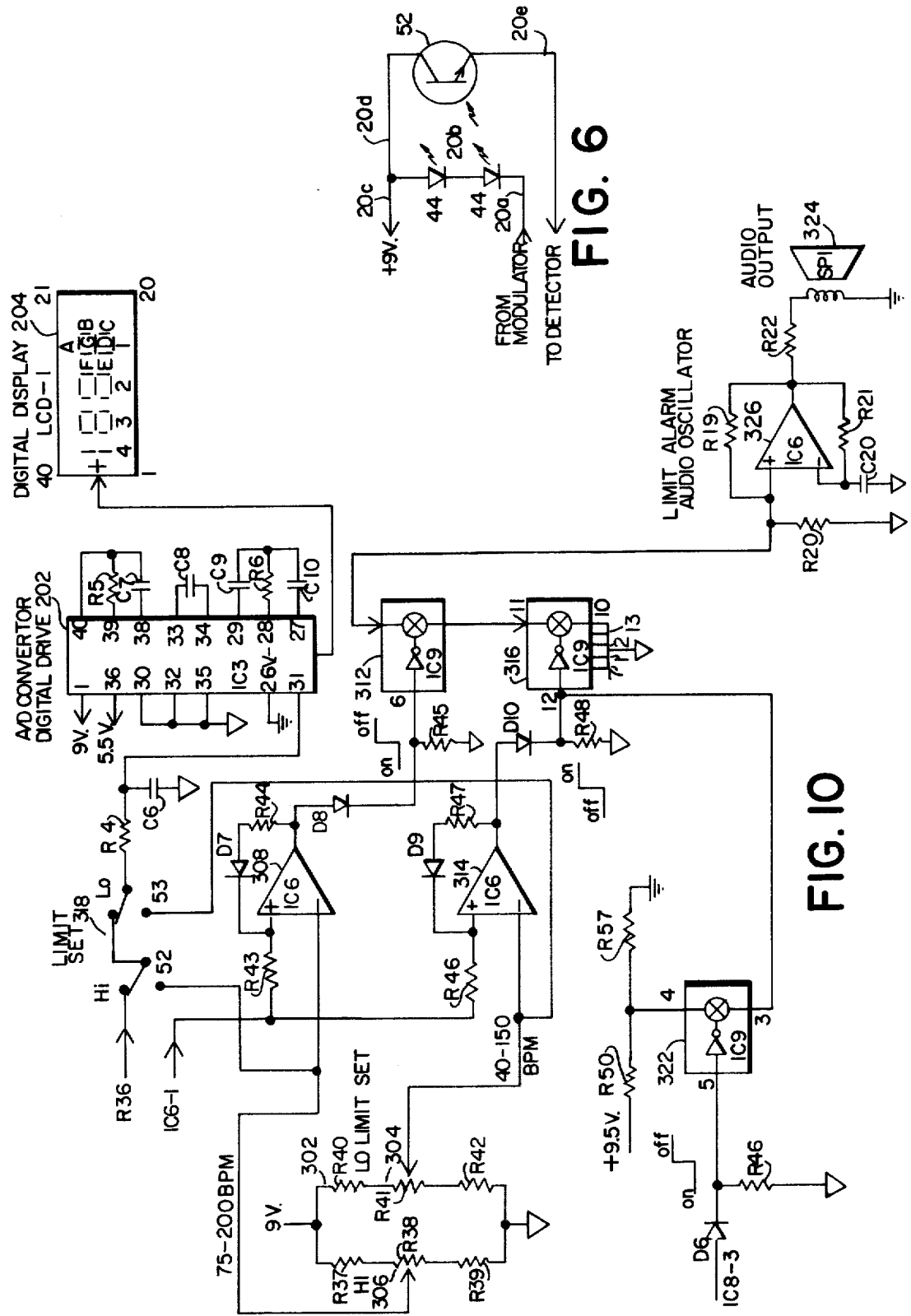
FIG. 6 is a circuit diagram of the emitting/detector elements of the sensor assembly.

The physical design of sensor assembly 14 is shown in detail in FIGS. 3, 4 and 5. The electrical circuit is shown in FIG. 6. Referring now to FIG. 3, a side view of the sensor assembly is shown. A light shield plate 40 and a sensor plate 50 comprise the two main parts of the sensor assembly. Both plates contain contain emitters 44a and 44b in housings 46a and 46b respectively whereas only the sensor plate 50 contains the detector 52 in housing 46c. In the present instance the detector 52 may be a photodetector for sensing light reflected or transmitted by the emitters. The two plates are pivoted about bolt 32. As shown in FIG. 4, tension to hold the two sensor plates 40 and 50 normally closed is maintained by a tab 34 on the end of spring 36 which is disposed around and along the length of bolt 32. The spring is locked in place by nut 37. The effect of the physical configuration and the spring is to bring the emitters and detector in close proximity to one another with enough clamping action provided by the spring so as to prevent the sensor assembly from moving when applied to the user's ear, for example. The pressure applying relation, however, is not so great to materially change normal flow of blood. The light shield prevents extraneous ambient light from entering into the detector 52.

Figure 2:
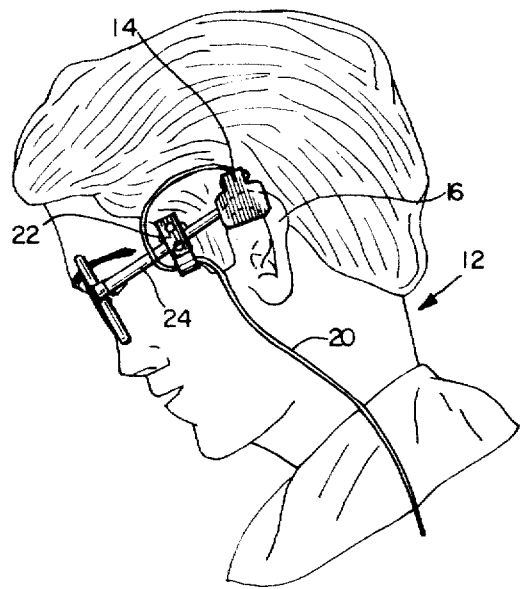
FIG. 2 is a close-up view of an exerciser wearing glasses showing the sensor assembly supported on the ear of the user and a clip for securing the cable to the eye glass frame.

The details of light shield plate 40 are shown in FIG. 4 and is characterized by a relatively large plate which, as shown in FIGS. 1 and 2 fits on the outer side of the subject's ear. Roughly centered within the light shield plate 40 is a small housing 46a containing the infrared emitting diode (IRED) 44a which physically fits up against the outer side of ear 16. The housings 46a, 46b and 46c as illustrated in FIG. 3 have confronting curved or arcuate faces so that the skin conforms to the housings providing good contact at the point of interest; namely, the desired area of the skin for monitoring blood flow. The housing 46a containing the IRED 44a along with leads 20a and 20b is attached to the light shield plate 40 with the leads fitted into a channel-like slot 48 of the arm of the light shield plate.

Turning now to FIG. 5 we see the details of sensor plate 50. This comprises a basically rectangular piece rotatably attached to clamp 30 so as to fit onto the inside of ear 16. At the upper end, two arcuate faced housings, disposed side by side are attached. One housing 46b contains a second IRED 44b and the other housing 46c contains a small infrared detector 52. Leads 20c, 20b and 20e are fitted into a channel-like slot of the arm of the sensor plate 50.

As shown in FIG. 6, the two IRED emitters are electrically connected in series but physically they are not located directly opposite one another. Rather they are offset slightly from one another with the outer one 44a aimed at detector 52 and directed at approximately the centerline between itself and detector 52. The net effect is to provide as large a signal variation as possible by both reflecting and transmitting a maximum amount of light during diastolic and a minimum amount of light during systolic conditions. By so doing, the overall sensitivity of the system is greatly increased and erratic behavior noted in prior art devices is essentially eliminated.

To keep the sensor assembly moment of inertia around the point of contact with ear and the mass as low as possible, all pieces are customarily fabricated from aluminum or other lightweight materials which minimizes motion artifacts caused by mass inertia considerations. Because the sensor electrical components are low voltage, low power units, light gauge wire can be used throughout. To preclude or minimize external light sources from entering the detector 52, all passive parts are customarily painted black to absorb light rays.

The total system, which as previously described consists of the Sensor Assembly 14, the Electronics Package Assembly 18, and the interconnecting cable 20, and its operation can best be understood by considering the functions defined in block diagram 7.

In normal operation, the subject's pulse rate is sensed by the ebb and flow of blood modulating the emitters/detector light path. The resulting modulated signal is processed and operated on to provide—analog, digital, and audio outputs of the subject's pulse rate. While the processing circuits taken individually may be a somewhat conventional approach to signal processing, the total design synthesizes these circuits into a system which provides a novel approach for obtaining a pulse rate signal which is highly tolerant of external noise sources.

Figure 7:
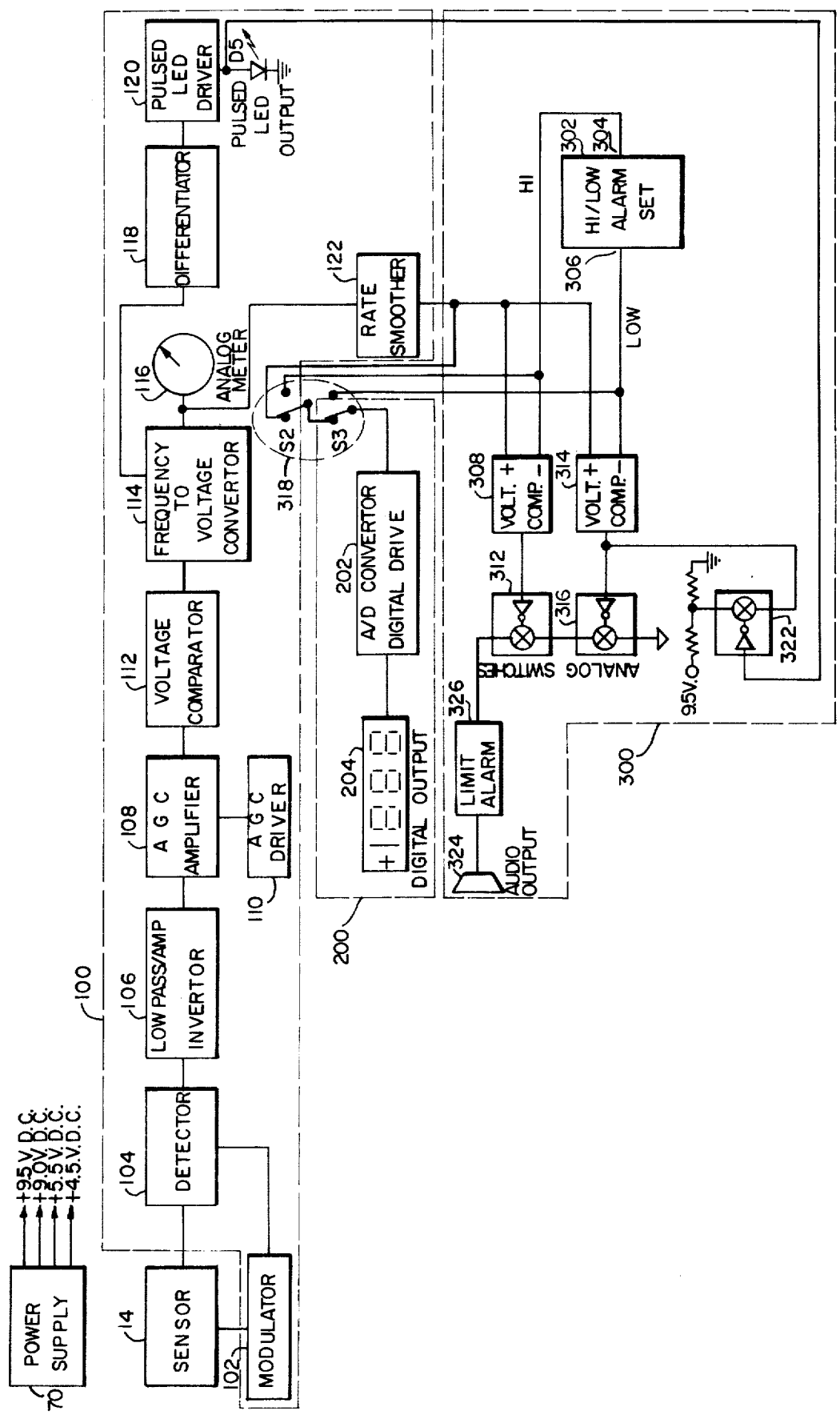
FIG. 7 is a block diagram of the sensor and electronic assembly of the present invention.
Figure 8:
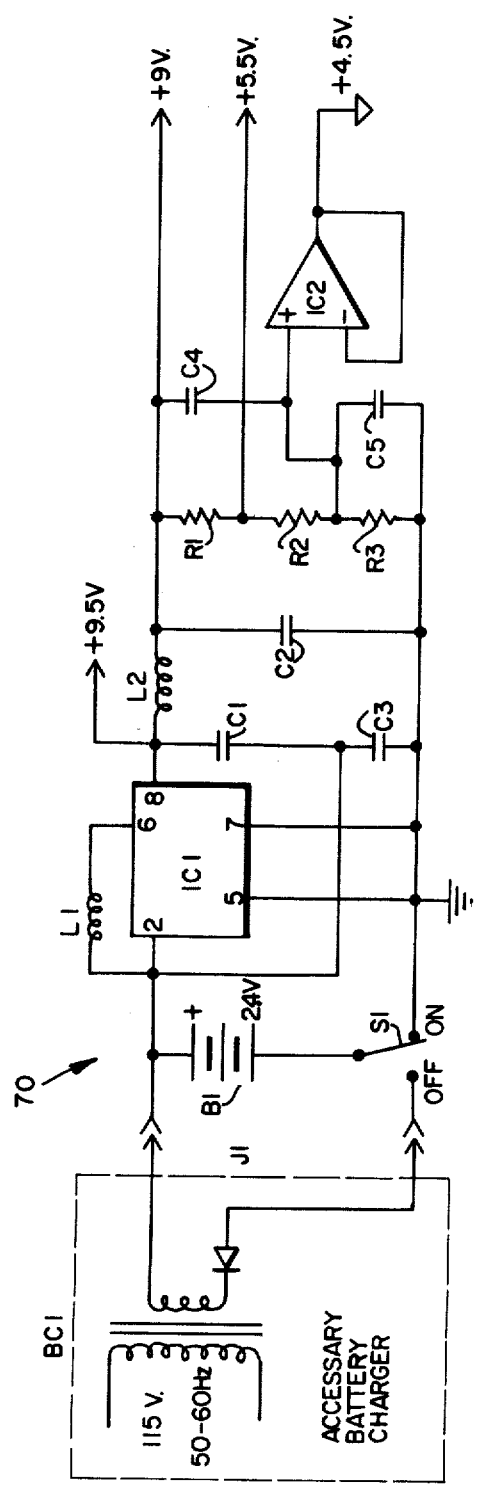
FIG. 8 is a detailed circuit diagram of the power supply.

Common to all circuits is power supply 70 shown in FIGS. 7 and 8. The power source is generally provided by a pair of 1.2 volt AA size, rechargeable nickel cadmium batteries. The power supply output consists of four DC voltages; 9.5 V, +9 V, 5.5 V and 4.5 V; required by the various integrated circuits. To extend battery life, low power BIFET operational amplifiers and CMOS integrated circuits are used wherever possible. Nickel cadmium batteries are also rechargeable and power supply 70 includes jack J1 to which a commercial AA battery charging system may be connected. The use of this system is facilitated by single pole double throw switch S1 which in the "off" position sets up the circuit for battery charging.

From block diagram of FIG. 7, the sensor assembly 14 emitters 44a and 44b are power strobed by modulator 102. The pulse train thus provided is in turn modulated by the relatively low frequency pulse rate of the subject. This composite signal is detected by detector 104 and then into low pass amplifier/inverter 106. This serves the function of stripping the subject's relatively low frequency low level pulse signal from the much higher frequency waveform. Automatic gain control 108 is provided to eliminate manual manipulation by the subject. The final signal processing converts the pulse signal to a constant amplitude square wave by comparator 112. This is then converted into an analog DC voltage by frequency to voltage converter 114 which is scaled so that the output correlates with the pulse rate. This can be displayed on a conventional 0-1 ma meter 116. Both the signal and an auxiliary signal from the frequency to voltage comparator 114 can be used to drive a digital display of pulse rate, a high/low limit alarm 300 as shown on FIG. 7, or a light blinking at the exerciser's pulse rate.

Having now described the sensor assembly details and the overall system, the following sets forth the details of the circuitry more specifically.

Both the pair of IREDs 44 and detector 52 operate from a common +9 volt DC supply which in the preferred embodiment is supplied from a battery power source (shown in FIG. 8). This voltage is brought in on conductor 20c which feeds into inner side IRED. This voltage is then fed via conductor 20b to series connected outer IRED. The 9 V current is switched on and off by a signal at a frequency of 200 HZ coming in on conductor 20a from modulator 102, shown in FIGS. 7 and 9. The function of this will be discussed herein below.

The +9 volts is further supplied to sensor 52 by an internal jumper 20d, as shown in FIG. 5. The sensor output, as stated hereinabove, is an oscillating DC voltage in which the low frequency heart beat pulse rate oscillation is impressed onto the much higher frequency oscillatory output generated by IREDs 44 switching on and off. The net effect is in much the same manner as a carrier wave is modulated in a radio circuit. This modulated output is carried by conductor 20e to analog logic circuit 100 shown in block form in FIG. 7 and schematically in FIG. 9.

Turning now to FIG. 7, we see a block diagram of the circuitry including analog, logic, digital output and audio alarm portions of module 18. This should be read in conjunction with FIGS. 9 and 10 which are detailed circuit diagrams.

Common to all subsystems is power supply 70 shown in FIGS. 7 and 8. In the preferred embodiment this comprises a pair of 1.2 volt AA nickel cadmium batteries B1, working in conjunction with power controller IC1 and operational amplifier IC2 to provide the +4.5, +5.5, +9 and +9.5 VDC outputs required by the various integrated circuits used. To extend battery life, low power BIFET operational amplifiers and CMOS integrated circuits should be used wherever possible. Nickel cadmium batteries are also rechargeable and power supply 70 includes a jack, J1, to which a commercial AA battery charging system may be connected. The use of this system is facilitated by single pole double throw switch S1 which in the "off" position sets up the circuit for battery charging.

Figure 9:
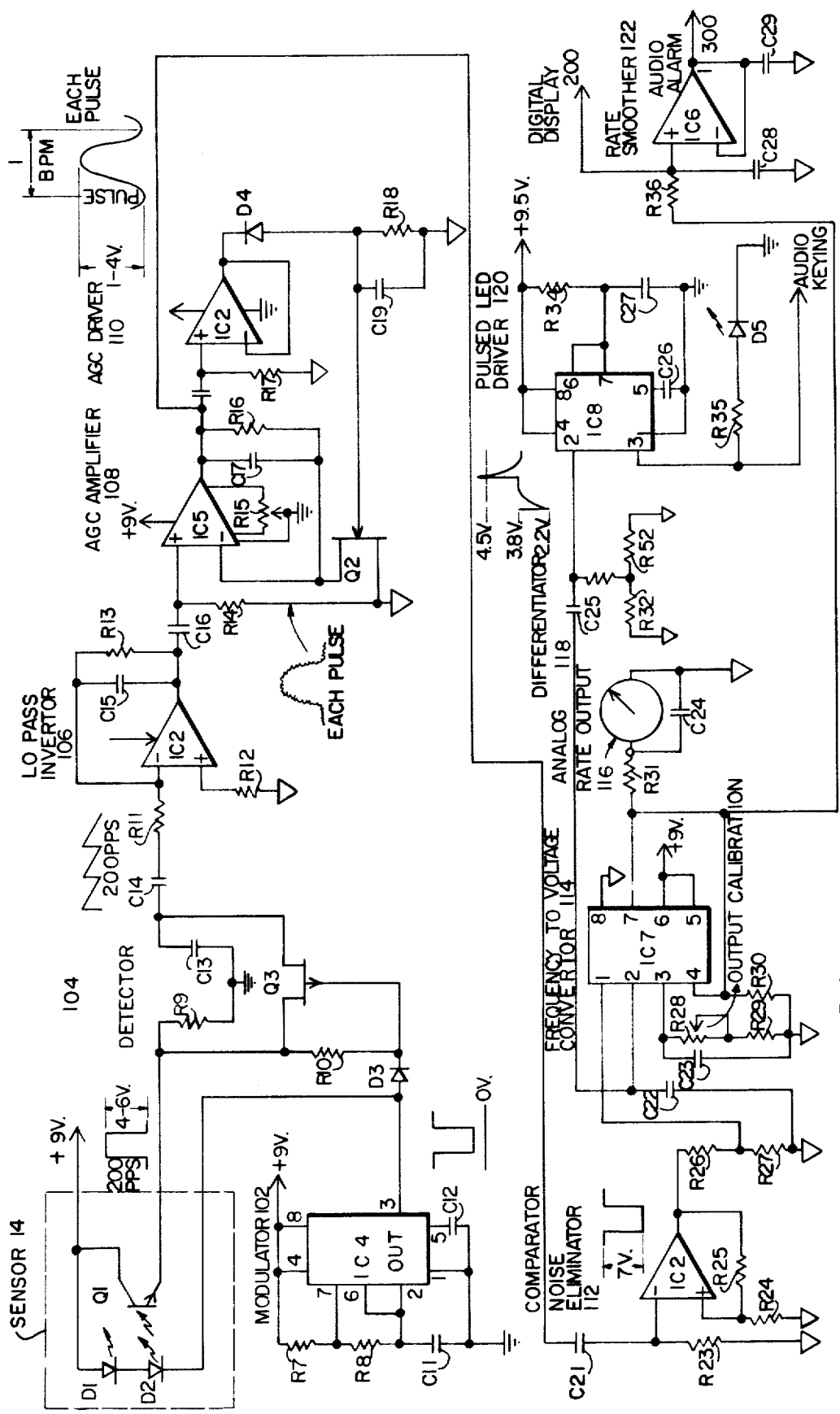
FIG. 9 is a detailed circuit diagram of the analog portion of the sensor and electronic package assemblies.

Looking again at FIGS. 7 and 9, we see that analog logic subsystem 100 comprises the basic signal processing circuitry common to all embodiments of the invention. As shown, it comprises an astable oscillator/modulator 102 which drives infrared emitting diodes 44a and 44b at a frequency of 200 HZ in the manner described hereinabove. The output is an asymmetric square wave having an output pulse width of about 50 microseconds.

The output of modulator 102 is also used to gate the P-channel field effect transistor (FET) Q3 in detector 104. Diode D3 is biased so that modulator 102 output is fed to the gate of FET Q3 only when the IREDs are not being pulsed. This turns FET Q3 off when no signal is produced in sensor 14 and on when the signal is produced. As a result, the charge on capacitor C13 develops a voltage equal to the peak of the square wave signal coming from photodetector 52. This voltage varies in an inverse proportion to the blood density in the ear. Superimposed on this varying voltage is a sawtooth waveform of a magnitude greater than the varying voltage itself; the sawtooth being at the frequency of modulator 102 and caused by leakage through FET Q3 when in the off state. The combination pulse signal and sawtooth are fed into low pass amplifier/invertor 106. This serves the function of stripping the relatively low frequency pulse signal from the much higher frequency sawtooth. To eliminate all extraneous sources of noise, the upper cutoff frequency of amplifier 106 is set at 0.3-0.4 HZ which is adequate to pass the exerciser pulse oscillations but very little else.

The input to automatic gain contol (AGC) amplifier 108 cuts off frequencies below 0.5 HZ which limits DC level shifts caused by motion artifacts. The limited signal from amplifier 106 is then fed into amplifier 108 which has a high cut off frequency of about 1.7 HZ. The combination of all the low and high cut off frequencies eliminates motion artifacts, noise and the IRED modulation frequency superimposed on the pulse waveform. Since the blood pulse signal is also affected by these cut off frequencies, the AGC amplifier 108 working in conjunction with AGC driver 110 restores that signal to a needed operational level. AGC amplifier 108 is also an important factor in generating relatively constant amplitude signals arising from different users.

The final signal processing converts the demodulated exerciser pulse rate oscillation from a sine wave to a constant amplitude square wave by comparator 112. This is then converted into an analog DC voltage by frequency to voltage convertor 114, the output from which can easily be scaled so that it correlates with pulse rate. This voltage can be displayed on a conventional 0-1 ma meter, 116, to produce a simplified low cost system.

The square wave output portion of frequency to voltage convertor 114 is used for timing purposes. After processing by differential circuit 118 to convert the square wave to a dual spike, the negative signal is used as a trigger for pulsed LED driver 120. The negative trigger signal is used so that when the output of driver 120 is fed into a conventional light emitting diode D5, the diode flashes in sync with the exerciser's pulse. Diode D5 is usually positioned so that the exerciser can easily observe it blinking on and off in response to the intermittent output of driver 120.

The output of the frequency to voltage converter 114 is also fed into rate smoother 122. This limits the digital output display 204 and audio alarm 200 from following the unimportant, beat-to-beat heart rate changes. These unimportant changes are automatically eliminated from meter 116 due to its internal damping.

Turning now to FIGS. 7 and 10 we see the details of the digital output and audio alarm subsystem of the subject invention. Of the two, the digital output 200 is the simpler.

Although there are numerous circuit designs for digitizing an analog voltage, recent development now permit this to be done quite simply. In the preferred embodiment the analog voltage output of rate smoother 122 is fed directly into a single chip 3½ digit analog to digital convertor 202. The output of this unit, which in the preferred embodiment is an Intersil ICL 7106, is a 24 BIT signal with the correct power and impedance levels to drive a signed 3½ digit, seven bar liquid crystal display (LCD) 204. Since the output of convertor 114 is scaled, the readout is directly in pulse beats per minute. While LED or other types of readout devices can be used quite easily as the circuit may require, LCD units are particularly preferred because of their distinct superiority in terms of low power consumption on extended use.

Turning again to FIGS. 7 and 10 we now consider audio alarm 300. This serves the function of allowing the user to set maximum and minimum pulse beat rates as a warning of over-exercise and of inadequate exercise levels. These settings are made in rate limit setter 302 which comprises a pair of variable resistance circuits 304 and 306 through which 9 VDC is dropped to 4.5 VDC. The center tap of potentiometer R38 sets a high level compared in high comparator 308 to the output from rate smoother 122. When this pulse rate exceeds the high set rate (between 75 and 200 beats per minute) fed into it, comparator 308 goes from low to high and turns off normally on analog switch 312. When this happens, the input to limit alarm audio oscillator 326 is no longer grounded and it oscillates so that a steady audio alarm is emitted by speaker 324.

A similar activity takes place with the low pulse rate signal. This is set by potentiometer R41 to provide a signal equal to a pulse beat rate in the range of 40 to 150 beats per minute. This too is compared with the output of rate smoother 122 in low comparator 314. Here, however, the low rate analog switch 316 is reversed so that when comparator 314 is low, the analog switch is off allowing oscillator 326 to drive speaker 324. In order to identify the low alarm from the high alarm audio signal, analog switch 322 is added to pulse analog switch 316 in sync with the heart beat. This results in a pulsed audio alarm which is synchronized with heart rate. When the low rate limit is exceeded, comparator 314 goes high and analog switch 316 is switched to the on position turning off oscillator 326. When the low level comparator 314 is high, analog switch 322 can no longer pulse the low rate analog switch 316.

As a result, when the level of the low rate potentiometer R41 is set lower than the high rate potentiometer R38, a pulsed audio tone will be heard if the user's heart rate is below the low rate set, no sound will be heard when the user's heart rate is between the low rate set and the high rate set, and a continuous tone will be heard when the user's rate exceeds the set high rate. Finally, both rate comparators 308 and 314 have built in hysteresis so that when the user rate just exceeds the set level, the alarm is not switched on and off due to slight fluctuations in the rate or reference voltage.

It was noted above that the high and low pulse beat limits were user setable. This is done in connection with limit set 318 which comprises single pole double throw switches 52 and 53. In the normal position these provide a direct path from smoother 122 to digital convertor 302 as shown in FIG. 10. However, when 52 is switched, it shuts off the smoother 122 output voltage and shunts the high pulse beat set signal from the center tap of potentiometer R38 into digital convertor 302 for display. Switch 53 performs the same function with the low pulse beat set signal from potentiometer R41. These adjustments are readily made by making the center tap of the two potentiometers readily accessible from the outside casing of module 18.

The circuit diagram and present invention described herein may be described in other specific forms without departing from the spirit or essential attributes thereof, and accordingly, reference should be made to the appended claims rather than to the foregoing specification as indicating the scope of the invention.

What is claimed is:

1. A pulse monitoring system for detecting and displaying blood pressure pulses resulting from heartbeats, comprising sensing means adapted to be positioned in contact with body tissue to respond to changes in blood volume, said sensing means including detector means and at least two light emitters, one of said emitters being a light transmitting emitter positioned to transmit light through said body tissue to said detector means and the other being a light reflecting emitter positioned to reflect light therefrom to said detector means, said detector means sensing changes in said light transmitted and changes in said light reflected due to variations in tissue perfusion and producing an electrical signal corresponding to said changes, signal processing means for converting said electrical signal to pulse rate.

2. A pulse rate monitoring system as claimed in claim 1 wherein said emitters are power strobed to provide a pulsed output.

3. A pulse rate monitoring system as claimed in claim 1 including means for converting said response into a pulse rate output and wherein said display means comprises a digital output adapted to display pulse in heartbeats per minute.

4. A pulse rate monitoring system as claimed in claim 1 including means for converting said response into a DC signal proportional to pulse in heartbeats per minute and displayed on an analog meter.

5. A pulse rate monitoring system as claimed in claim 1 wherein said output means comprises a light emitting diode adapted to provide a visible output in sync with a heartbeat.

6. A pulse rate monitoring system as claimed in claim 1 wherein said emitters are mounted in light shielded housings, one of said emitters opposite said detector means directed approximately along the center line between itself and said detector means and said other emitter mounted next to said detector means to provide as large a signal variation as possible by both reflecting and transmitting a maximum amount of light into said detector means during diastolic conditions and a minimum amount of light into said detector means during systolic conditions.

7. A pulse rate monitoring system as claimed in claim 6 wherein said housings are pivotally mounted and biased so that said emitters and said detector means contact the body tissue with a predetermined pressure sufficient to provide good contact for efficient light transmission and reflection and without undue blockage of blood flow in said tissue contacted by said sensing means.

8. A pulse rate monitoring system as claimed in claim 1 including a cable connecting said sensing means and signal processing means to conduct said signals from said detector means to said signal processing means, and means for fixing the connecting cable with a relaxed loop adjacent the sensing means to isolate the sensing means from physical stresses imposed by the total-weight of said connecting cable and other forces acting on said connecting cable.

9. A pulse rate monitoring system as claimed in claim 1 including alarm means adapted to detect abnormally high or low pulse rate to provide an alert to such condition.

10. A pulse rate monitoring system as claimed in claim 9 wherein said alarm means comprises means for setting high and low pulse rate signals and audio alarm means actuatable whenever said high or low signals are exceeded.

11. In a pulse rate monitoring system for detecting and displaying pulses resulting from heartbeats, sensing means adapted to be positioned in contact with body tissue in the region of a blood flow path to respond to changes in blood volume, said sensing means including detector means and at least two light emitters, one of said emitters being a light transmitting emitter positioned to transmit light through said blood flow path to said detector means and the other being a light reflecting emitter positioned to reflect light from said blood flow path to said detector means, said detector means sensing changes in the light transmitted by said light transmitted and changes in said light deflected due to variation in tissue perfusion.

12. A pulse rate monitoring system as claimed in claim 11 wherein said signal processing means comprises circuit means operable to produce a high signal to noise pulse train including a modulator for strobing the detector output, a filter for limiting high and low responses from the detector and gain control for automatically adjusting the pulse train output level.

13. A pulse rate monitoring system as claimed in claim 11 wherein said emitters are mounted in light shielded housings, one of said emitters opposite said detector means directed approximately along the center line between itself and said detector means and said other emitter mounted next to said detector means to provide as large a signal variation as possible by both reflecting and transmitting a maximum amount of light into said detector means during diastolic conditions and a minimum amount of light into said detector means during systolic conditions.

14. A pulse rate monitoring system as claimed in claim 11 including a cable connecting said sensing means and signal processing means to conduct said signals from said detector means to said signal processing means, and means for fixing the connecting cable with a relaxed loop adjacent the sensing means to isolate the sensing means from physical stresses imposed by the total weight of said connecting cable and other forces acting on said connecting cable.

15. A pulse rate monitoring system as claimed in claim 11 wherein said housings are pivotally mounted and biased so that said emitters and said detector means contact the body tissue with a predetermined pressure sufficient to provide good contact for efficient light transmission and reflection and without undue blockage of blood flow in said tissue contacted by said sensing means.

* * * * *